(12) United States Patent
Habib (10) Patent No.: US 11,696,850 B2
(45) Date of Patent: Jul. 11, 2023

(54) EYE THERMAL COMPRESS

(71) Applicant: Umay Care Holdings Inc., Edmonton (CA)

(72) Inventor: Ali Habib, Edmonton (CA)

(73) Assignee: Umay Care Holdings Inc., Edmonton (CA)

( * ) Notice: Subject to any disclaimer, the term of this patent is extended or adjusted under 35 U.S.C. 154(b) by 995 days.

(21) Appl. No.: 16/092,836

(22) PCT Filed: Apr. 13, 2017

(86) PCT No.: PCT/CA2017/050464
§ 371 (c)(1),
(2) Date: Oct. 11, 2018

(87) PCT Pub. No.: WO2017/197496
PCT Pub. Date: Nov. 23, 2017

(65) Prior Publication Data
US 2019/0125579 A1    May 2, 2019

Related U.S. Application Data

(60) Provisional application No. 62/321,976, filed on Apr. 13, 2016.

(51) Int. Cl.
*A61F 7/02* (2006.01)
*A61F 7/00* (2006.01)
*A61F 9/04* (2006.01)

(52) U.S. Cl.
CPC ............... *A61F 7/02* (2013.01); *A61F 7/007* (2013.01); *A61F 9/04* (2013.01);
(Continued)

(58) Field of Classification Search
CPC ...... A61F 2007/0004; A61F 2007/0075; A61F 2007/0086; A61F 2007/0093;
(Continued)

(56) References Cited

U.S. PATENT DOCUMENTS 3,768,485 A * 10/1973 Linick ..................... A61F 7/103
607/109
6,155,995 A * 12/2000 Lin .......................... A61F 7/02
601/148
(Continued)

FOREIGN PATENT DOCUMENTS

CN         1297719 A      6/2001
CN       103800128 A      5/2014
(Continued)

OTHER PUBLICATIONS

PCT International Search Report and Written Opinion, Application No. PCT/CA2017/050464, dated Aug. 1, 2017.
(Continued)

*Primary Examiner* — Kaitlyn E Smith
*Assistant Examiner* — Bradford C. Blaise
(74) *Attorney, Agent, or Firm* — MacMillan, Sobanski & Todd, LLC (57) ABSTRACT

An eye compress assembly includes two thermally adjustable heating and cooling device and a bridge connecting the two devices is provided. The thermally adjustable device is configured to apply thermal treatment against the eye region. Within the thermally adjustable heating and cooling device the thermoelectric element is powered by a battery. A power input port is provided in the bridge to connect into a power supply in order to recharge the battery.

20 Claims, 10 Drawing Sheets

(52) U.S. Cl.
CPC ............ *A61F 2007/0004* (2013.01); *A61F 2007/0075* (2013.01); *A61F 2007/0086* (2013.01); *A61F 2007/0228* (2013.01); *A61F 2007/0261* (2013.01)

(58) Field of Classification Search
CPC ...... A61F 2007/0228; A61F 2007/0261; A61F 7/007; A61F 7/02; A61F 9/04
See application file for complete search history.

(56) References Cited

U.S. PATENT DOCUMENTS

| | | | |
|---|---|---|---|
| 6,908,195 B2* | 6/2005 | Fuller | A61F 9/028 351/158 |
| 2003/0195438 A1 | 10/2003 | Petillo | |
| 2006/0200052 A1* | 9/2006 | Lin | A61H 5/00 601/70 |
| 2007/0282405 A1* | 12/2007 | Wong | A61F 7/12 607/104 |
| 2012/0222192 A1* | 9/2012 | Carey | A61F 7/02 2/171.2 |
| 2013/0172829 A1 | 7/2013 | Badawi | |
| 2014/0277303 A1 | 9/2014 | Biser et al. | |
| 2015/0057701 A1* | 2/2015 | Kelleher | A61H 23/0245 606/204.15 |
| 2015/0190607 A1* | 7/2015 | Sugio | A61F 9/04 600/27 |
| 2016/0000600 A1* | 1/2016 | Lee | A61F 7/00 607/109 |
| 2017/0014300 A1* | 1/2017 | Dippo | A61F 7/034 |
| 2021/0128058 A1* | 5/2021 | Habib | A61B 5/01 |

FOREIGN PATENT DOCUMENTS

| | | |
|---|---|---|
| CN | 104207878 A | 12/2014 |
| CN | 104473759 A | 4/2015 |
| CN | 104510558 A | 4/2015 |
| CN | 205698210 U | 11/2016 |
| CN | 106214330 A | 12/2016 |
| DE | 202013102909 U1 | 11/2013 |
| JP | 2006198249 A | 8/2006 |
| WO | 2015030560 A1 | 3/2015 |
| WO | 2018044877 A1 | 3/2018 |

OTHER PUBLICATIONS

The Extended European Search Report, Application No. 17798433.3, dated Jun. 24, 2020.
Supplementary European Seach Report, Application No. 17798433.3, dated Feb. 6, 2020.
The machine translation of the document "First Office Action for Chinese Application No. 20178002325", dated Jul. 1, 2020; pp. 1-9.

* cited by examiner

EYE THERMAL COMPRESS

FIELD OF THE INVENTION

The invention is directed to thermal health devices, and more specifically to thermal health devices for application to eyes.

BACKGROUND OF THE INVENTION

In the human eye, the tear film covering the ocular surfaces is composed of three layers. The innermost layer in contact with the ocular surface is the mucus layer. The mucus layer is comprised of many mucins. The middle layer comprising the bulk of the tear film is the aqueous layer. The aqueous layer is important in that it provides a protective layer and lubrication to prevent dryness of the eye.

Dryness of the eye can cause symptoms such as itchiness, burning, and irritation, which can result in discomfort. The outermost layer is comprised of many lipids known as "meibum" or "sebum." This outermost lipid layer is very thin, typically less than 250 nm in thickness. The lipid layer provides a protective coating over the aqueous and mucus layers to limit the rate at which these underlying layers evaporate. A higher rate of evaporation of the aqueous layer can cause dryness of the eye. Thus, if the lipid layer is not sufficient to limit the rate of evaporation of the aqueous layer, dryness of the eye may result. The lipid layer also lubricates the eyelid during blinking, which prevents dry eye. If the lipid layer can be improved, the rate of evaporation is decreased, lubrication is improved, and partial or complete relief of the dry eye state is achieved.

Environmental conditions can contribute to dry eye, for example, exposure to smoke, wind and dry climates can increase tear evaporation resulting in dry eye symptoms. Failure to blink regularly, such as when staring at a computer screen for long periods of time, can also contribute to drying of the eyes.

Dry eye can also be caused by a condition known as meibomian gland dysfunction (MGD). Symptoms of MGD include dryness, burning, itching, stickiness, watering, light, sensitivity, red eyes, foreign body fensation, chalazions, styes, and intermittent blurry vision. Known treatments for MGD generally apply significant heat in order to melt, loosen, or soften obstructions and/or occlusions in the meibomian glands.

The application of hot and/or cold compresses is a known therapeutic treatment for some physical ailments. Some conventional methods of thermal compress therapy include a user holding a cloth (e.g., a washcloth) under hot or cold running water and then applying the moist, temperature-adjusted cloth to the desired body part. In some such instances, the cloth is maintained in contact with the desired body part through manual intervention (e.g., the user holds the cloth in place).

In other conventional methods, a silica gel (e.g., sodium acetate) pack can be heated or cooled, to apply thermal energy to or remove thermal energy from the eye region of the user. In some embodiments, the thermal packs can be included in a device that includes a container or frame configured to support the thermal packs and a strap system configured to retain the thermal packs in a fixed position relative to the eye region of the user. The anatomy of the eye region, however, can result in challenges to the application of thermal packs. For example, the contour of the eye region can result in challenges to placing the thermal packs with a relatively consistent and comfortable amount of force. As such, the level of discomfort and/or ineffective application or removal of thermal energy can, in some instances, deter a user from using some such devices.

Regarding electrical heaters, one conventional eye treatment is described in U.S. Patent Pub. No. 2007/0060988. The heater it describes applies heat by using an electrical signal requiring the use of a thermocouple and sophisticated feedback control system to monitor and adjust the electrical signal to maintain heat between 43 and 47° C. to one eye for between 1 and 10 minutes. Furthermore, the device uses a screw to adjust pressure on the eye. Since it requires 1) a threaded shaft or screw adjustment, 2) elevated heat, and 3) precise thermal regulation independent of temperature, the time of treatment, actual temperature, and pressure on the eye must be administered and monitored by a medical physician or technician to avoid burning the eyelid or damaging the eye itself.

Another conventional heater is described in U.S. Pat. No. 4,261,364. The heater it describes uses a battery operated surgical heater that warms a compress resembling an eye patch for post-ophthalmic surgery patients. The heater is strapped to a surgical compress that applies heat to a patient's eye socket. Since the heater 1) is in molded plastic not integrated with the compress, 2) is battery operated, 3) uses wiring for a heating element, and 4) heats a compress rather than an eyelid, the result is an uncomfortable, uncontrolled heat source that cannot carefully control the temperature that reaches the eyelid itself. Due to these factors, the time of treatment, actual temperature, and pressure on the eye must also be administered and monitored by a medical physician or technician to avoid burning the eyelid or damaging the eye itself.

Thus, improved apparatus, systems and methods for providing thermal therapeutics to the eye region are needed.

SUMMARY OF THE INVENTION

The present application relates generally to apparatuses, systems and methods for applying thermal treatment to the eye region by the application or removal of thermal energy.

According to an embodiment of the present application, there is provided an eye thermal compress assembly comprising: two thermal treatment units each having an upper shell and a lower shell, the two thermal treatment units generating thermal energy to provide a heated or cooled lower surface; a bridge connecting the two thermal treatment units. In some embodiments, the eye thermal compress assembly is used with the user lying face up and the eye thermal compress assembly resting on the user's eyelids. In some embodiments, an optional attachment means is provided for attaching the eye thermal compress assembly to the head, allowing use of the eye thermal compress assembly when the user is not lying down.

As well, according to an embodiment of the present application there is provided a thermal treatment unit, the thermal treatment unit comprising: an upper shell; a mounting board; a lower shell; a thermoelectric cooler (TEC) for generating thermal energy; a printed circuit board (PCB) for controlling the TEC; a heatsink for dissipating thermal energy into the upper shell.

According to an embodiment of the present disclosure, there is provided an eye thermal compress assembly comprising: two thermal treatment units, the two thermal treatment units generating thermal energy to provide a heated or cooled treatment surface for the eyelids of a user when worn; and a bridge connecting the two thermal treatment units.

According to an embodiment of the present disclosure, there is provided a thermal treatment unit, comprising: an upper shell; a lower shell; a mounting board; a thermoelectric cooler (TEC) for generating thermal energy; a controller for controlling the TEC; a heatsink for dissipating thermal energy into the upper shell; wherein the TEC, the heatsink and the controller are contained with inside the upper shell and the lower shell.

BRIEF DESCRIPTION OF THE DRAWINGS

Embodiments of the present invention will now be described by way of example with reference to attached figures, wherein.

DETAILED DESCRIPTION OF EMBODIMENTS

Reference will be made below in detail to exemplary embodiments of the invention, examples of which are illustrated in the accompanying drawings. Wherever possible, the same reference numerals used throughout the drawings refer to the same or like parts.

Figure 1:
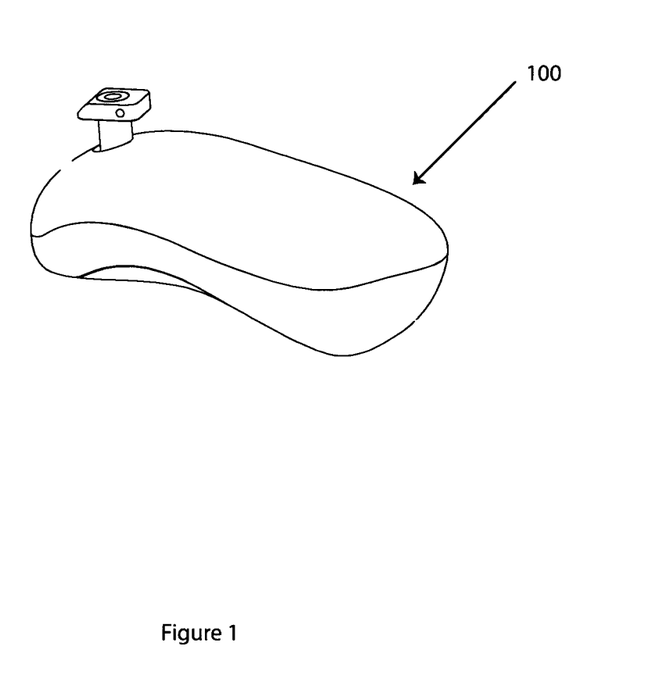
FIG. 1 illustrates a side view of one assembled thermal treatment unit.

FIG. 1 illustrates a side view of an assembled thermal treatment unit 100.

Figure 2:
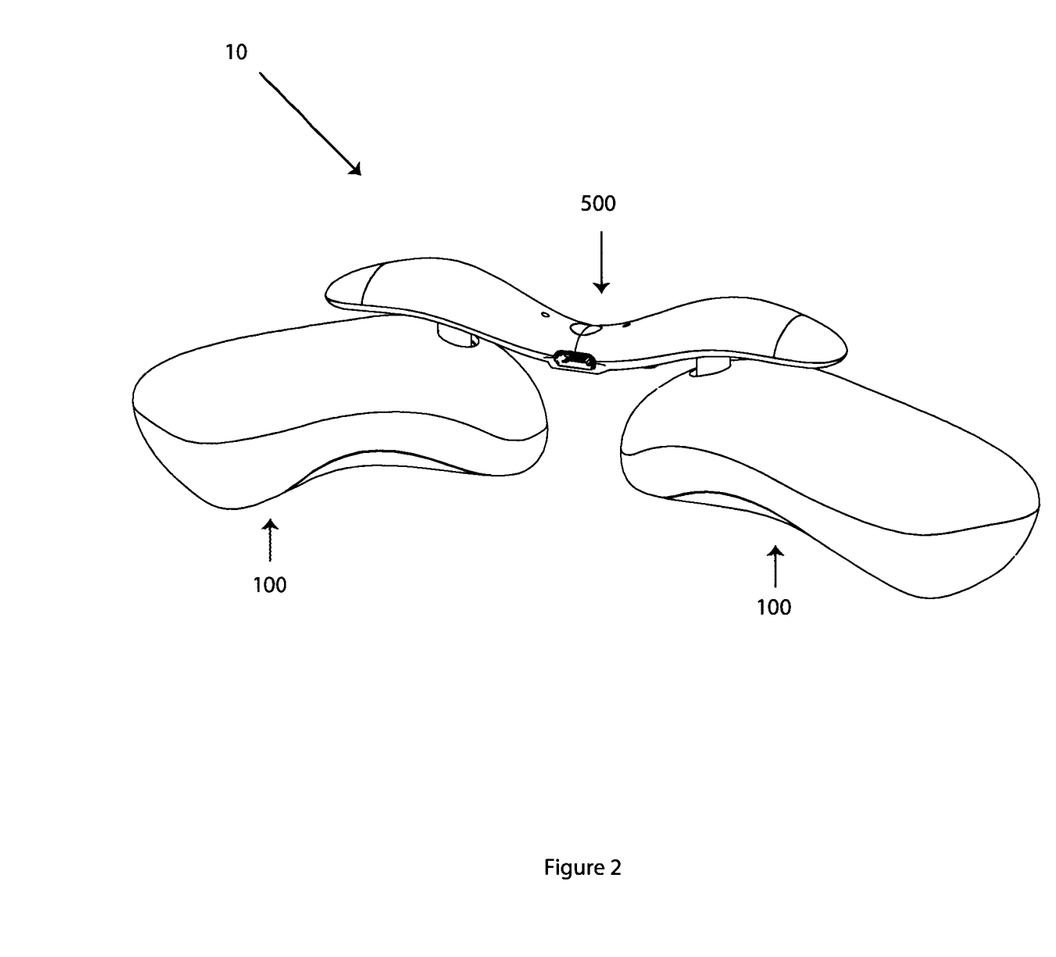
FIG. 2 illustrates a side view of an eye thermal compress assembly comprising two thermal treatment units and a bridge.

FIG. 2 illustrates a side view of the eye thermal compress assembly 10 according to an embodiment. The eye thermal compress assembly 10 includes two thermal treatment unit 100 connected by a bridge 500, so that the eye thermal compress assembly may apply heat therapy or cold therapy to both eyes at the same time if desired. In some embodiments, the user can choose to use either or both of the thermal treatment units at a time. The two thermal treatment units are identical to or as mirror image to each other. In one embodiment, the eye thermal compress assembly 10 is used while the user is lying face up and the thermal treatment unit 100 rests on the eyelids of the user without using any means to attach the eye thermal compress assembly 10 to the head of the user. This prevents too much pressure on the eyelids. It may also improve safety because it allows the eye thermal compress assembly to slide off the user's face when the user falls asleep. In some embodiments, an optional attachment means is used to secure the eye thermal compress assembly 10 in place in operation. The attachment means may be made from a flexible material such as neoprene that allows the attachment means to stretch. With the optional attachment means, the eye thermal compress assembly 10 does not require the user to lie down when using the eye thermal compress assembly 10. In some embodiments, there is provided an optional flexible band attached to the ends of the attachment means for attaching the eye thermal compress assembly 10 around a human head in operation more securely. The eye thermal compress assembly 10 does not require a medical physician or technician for administration and is adjustable for different wearers.

An optional moistened pad can be used between user's closed eyelid(s) and the thermal treatment units 100. Any suitable moistened pad known in the field may be used. In some embodiment, the moistened pad may be made of a fibrous non-woven fabric or other soft cloth material. In some embodiments, the moistened pad 220 is sized for a typical adult. In some embodiments, ointment may be provided on the moistened pad. In some embodiments, one or more pharmacological agent is provided in the pad. In some embodiments, the moistened pad is removably attached to the lower surface of the thermal treatment unit 100.

Figure 3:
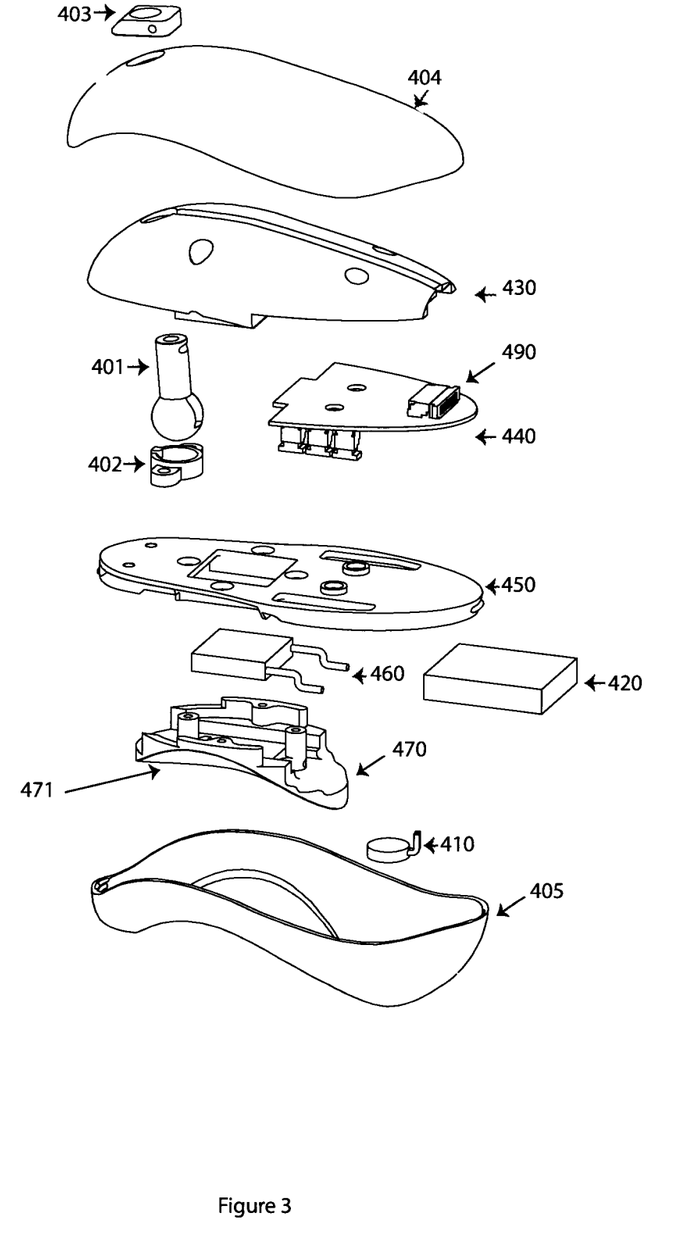
FIG. 3 illustrates an exploded view the thermal treatment unit according to an embodiment of the present application.

FIG. 3 illustrates an exploded view of the one of the unassembled thermal treatment unit 100. The thermal treatment unit 100 includes an upper shell 404, a heatsink 430, a lower shell 405 which forms a lower surface and which contacts a portion of a user's face, a mounting board 450, a haptic motor 410, a battery 420, a component 470, thermoelectric cooler (TEC) 460, a first PCB 440, a first receptacle 402, a connector 401 and a second receptacle 403.

When in operation, the lower shell 405 is close to the face of the user while the upper shell 404 is away from the face of the user. The heatsink 430 is close to the upper shell 404. In some embodiments, the heatsink 430 is disposed next to the upper shell 404 and the upper part of the heatsink 430 is shaped to fit the interior of the upper shell 404.

A pin connection component 490 may be used to connect the TEC 460 to the first PCB 440 by electrical wire (not shown). In some embodiments, the battery 420 is connected to the first PCB 440. The first PCB 440 may be used to control the battery 420 and TEC 460 during use. In some embodiments, the PCB 440 may control charging of the battery 420. The first PCB 440 may be connected to the battery 420 and TEC 460 by any suitable means known in the field, for example, by using electrical wires (not shown). The battery 420 may be rechargeable and/or replaceable. In a preferred embodiment, the battery is rechargeable and fixed. The battery 420 provides power to the TEC 460.

In some embodiments, the first PCB 440 may be connected to the haptic motor 410. The haptic motor 410 may be used to provide notifications to the user by way of vibration. The haptic motor 410 may be placed anywhere within the treatment unit so long as it can provide the notification. In one embodiment, the haptic motor 410 is attached to the side of the lower shell 405 that is interior to the thermal treatment unit 100 by adhesive. The haptic motor 410 may be attached by any other means known in the field. For example, a structure may be configured within the thermal treatment unit 100 to receive the haptic motor 410.

The mounting board 450 is used to secure the different components within the thermal treatment unit 100, for example, the PCB 440. In some embodiments, a hole is configured in the mounting board 450 so that the upper part of the TEC 460 passes through the hole to be in contact with the lower part of the heatsink 430. The heatsink 430 is used to draw heat away from the TEC 460 during cooling treatment. In some embodiments, the lower part of the heatsink 430 may be formed to maximize the contact area with the TEC 460. In some embodiments, the battery 420 is attached to the bottom of the mounting board 450 by any suitable means known in the field. In some embodiments, the battery 420 is attached to the mounting board by adhesive.

The mounting board 450 is also used to fixedly receive a first receptacle 402. The first receptacle 402 is for receiving the lower end of the connector 401. In a preferred embodiment, the surface of the first receptacle 402 for receiving the lower end of the connector 401 is partially spherical, while the lower end of the connector 401 is ball-shaped, so that the lower end of the connector 401 forms a ball joint structure with the first receptacle 402. In some embodiments, the upper part of the connector 401 is a stem that extends through holes in the heatsink 430 and the upper shell 404. In some embodiments, the connector 401 is hollow to allow electrical wires therethrough to connect the first PCB 440 to the bridge 500.

In some embodiments, the component 470 has a treatment surface 471 that is in contact with the eyelid when the thermal treatment unit 100 is in operation. In some embodiments, the treatment surface 471 is eye shaped and sized for a typical adult. In a preferred embodiment, the treatment surface 471 is smooth. The smooth treatment surface 471 may be made of metal, plastic, rubber, textile or any other suitable material. Preferably, the smooth treatment surface 471 is made of metal, selected from steel, stainless steel, copper, silver, gold and aluminum. In some embodiments, the lower shell 405 has a hole configured to expose the surface 471 to the exterior of the lower shell 405 when the thermal treatment 100 is assembled, such that the surface 471 is in contact with the eyelid when the thermal treatment unit 100 is in operation.

In some other embodiments, the lower shell 405 is configured with an eye shaped portion sized for a typical adult on the lower exterior surface of the lower shell 405. The eye shaped portion is in contact with the closed eyelids when the treatment unit 100 is in operation to provide heating or cooling treatment to the eyes. In such embodiments, the surface of the lower shell 405 that is interior of the lower exterior surface is in contact with the lower surface of component 470 to receive heating or cooling from the TEC 460.

The component 470 may also be configured to provide a structure to receive the TEC 460 therein so that the TEC 460 is close to the smooth treatment surface 471 and that the TEC 460 will not move freely inside the thermal treatment unit 100. In some embodiments, the structure provided is a groove to fit the lower part of the TEC 460 therein. In some embodiments, when the thermal treatment unit 100 is assembled, the component 470 is fixedly attached to the mounting board 450. The attachment can be by any suitable means known in the field. In preferred embodiments, the attachment is by adhesive and/or screws.

In operation, the thermal treatment units 100, which are battery powered, are placed over a closed outer eyelid to provide controlled heat or cold therapy. The thermal elements 100 may be made of a smooth material that is safe for placement against the skin. The thermal treatment unit 100 may include redundant temperature sensors (not shown) to ensure precise temperature control. As well, the first PCB 440 may identify a minimum and maximum temperature that may be generated by the thermal treatment unit 100 to ensure that the thermal elements are within a safe temperature range for use against unprotected skin. The thermal treatment unit 100 transfers thermal energy (e.g. hot or cold) supplied from a thermoelectric chip, such as the TEC 460 and directs the thermal energy via component 470 towards the user's eyes and eyelids. The TEC 460 generates thermal energy within the thermal treatment unit 100. The TEC 460 provides heating or cooling by means well-known in the field.

Figure 4:
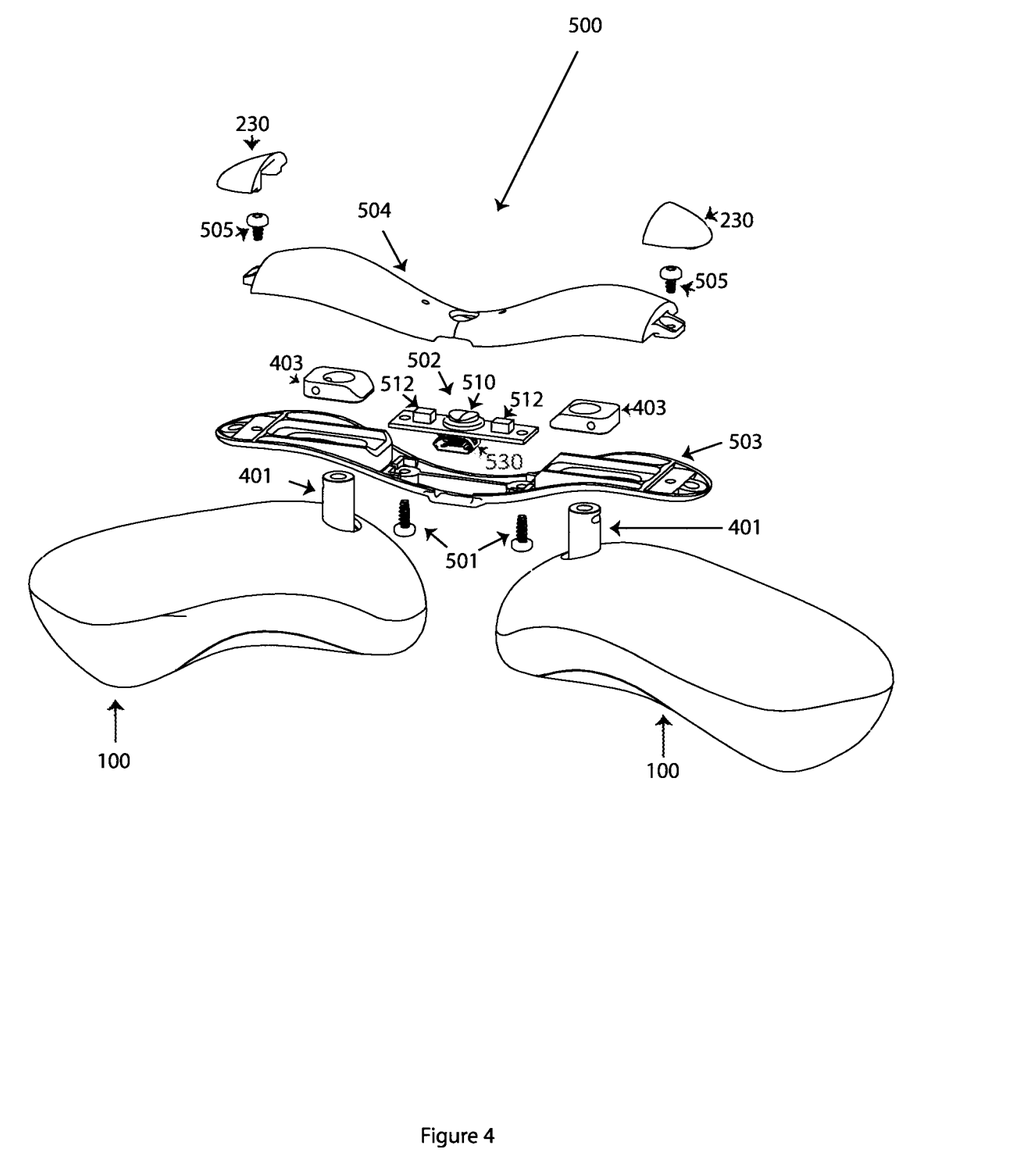
FIG. 4 illustrates a side exploded view of the bridge.
Figure 5:
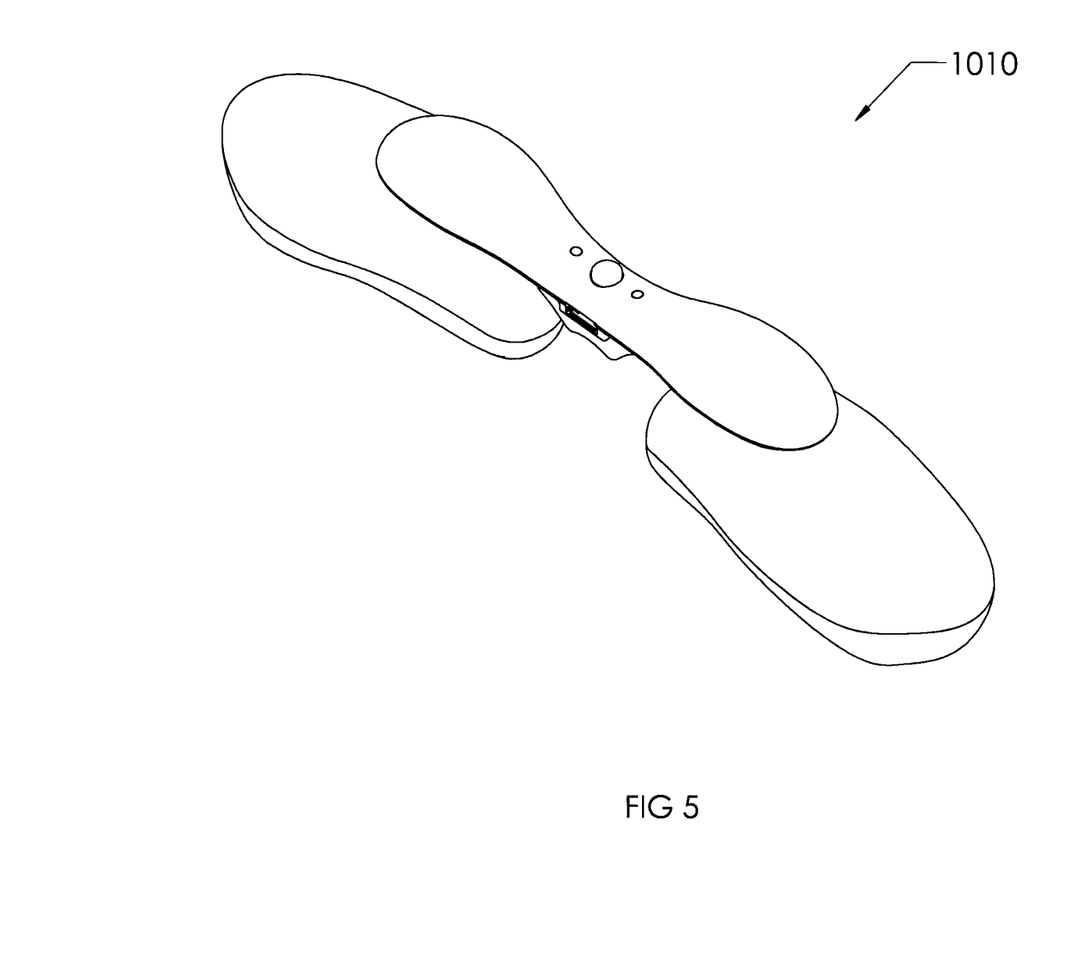
FIG. 5 is a perspective view of an eye thermal compress assembly according to another embodiment showing two thermal treatment units connected by a bridge.
Figure 6:
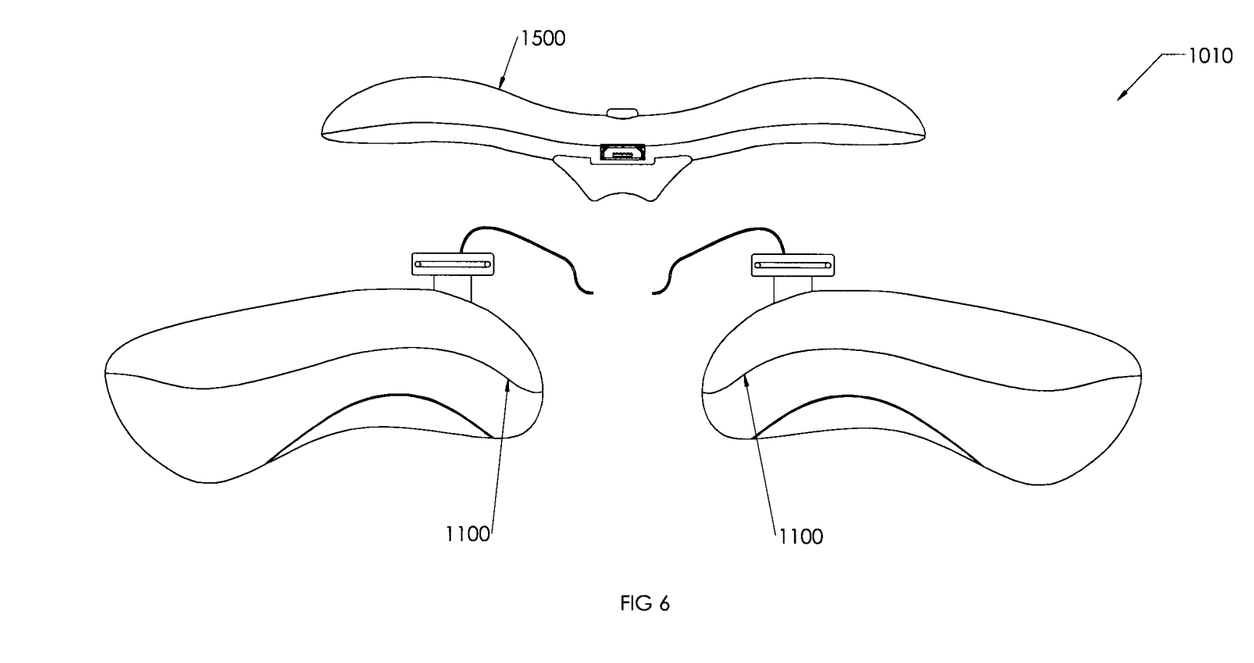
FIG. 6 is a side elevation view of the eye thermal compress assembly of FIG. 5 showing the two thermal treatment units detached from the bridge.

FIG. 4 illustrates a side exploded view of bridge 500. The Bridge 500 connects the two thermal treatment units 100. The bridge 500 comprises an upper shell 504 and a lower shell 503. The upper shell 504 and the lower shell 503 can be connected by any suitable means known in the field. For example, FIG. 4 shows that they are connected by screws 505 and the screws 505 are then covered with screw covers 230. The two thermal treatment units 100 are also electrically connected to the bridge 500 so that the bridge 500 can be powered by at least one battery 420 in one of the thermal treatment units 100. The electrical connection can be by the electrical wires through the hollow connectors 401 as described earlier.

There are holes configured in the lower shell 503 so that the upper part of the connector 401 can extend through the holes. The upper end of 401 is then received within the second receptacle 403 so that the thermal treatment unit 100 is connected to the bridge 500. The two thermal treatment units 100 are fixedly or adjustably attached to the bridge 500. For example, if there is ball-joint structure between the connector 401 and the first receptacle 402, the connection would be adjustable in relation to the thermal treatment unit 100. In some embodiments, each of the holes in the lower shell 503 to receive each of the stems of the connectors 401 is a groove to allow movement of the upper part of the connector 401 so that the thermal treatment units 100 are adjustable in relation to the bridge, for example, to fit different sizes of faces of the users.

As well, the bridge 500 includes a power input port 530 for receiving an electrical cord to connect the bridge 500 with an electrical power supply, thus providing power for charging the batteries 420 of the thermal treatment units 100 and/or for operation of the bridge 500. When an electrical cord is not connected to the power input port 530 of the bridge 500, at least one of the batteries 420 of the two thermal treatment units 100 that are attached to the bridge 500 may provide power for the operation of the bridge 500. In some embodiments, the power input port 530 is a micro USB port.

The bridge may further comprise a controller 502 so that the power input port 530 can be fixed to the controller 502. Controller 502 comprises a processor, a memory for storing programs for instructing the processor, and input and output. The bridge 500 may further include a push button 510, which may also be fixed to the controller 502. The bridge 500 may further comprise at least one indicator light 512, which may also be fixed to the controller 502. In some embodiments, the button 510 and the light 512 are integrated. In some other embodiments, the button 510 and the light 512 are separate.

When the upper shell 504 and lower shell 503 are assembled, the controller 502 is fixedly sandwiched between the upper shell 504 and the lower shell 503. The upper shell 504 and lower shell 503 are so configured that when they are assembled the power input port 530 is exposed for receiving a power input cord. The upper shell 504 may have holes configured therein for exposing the switch 510 and the indicator light 512.

In some embodiments, the button 510 and indicator light 512 are electrically connected to the first PCB 440. Control signals and power can be sent to the first PCB 440 and battery 420, while power can be sent from either or both batteries 420 from the two thermal treatment unit 100 to the button 510 and the light 512. The connection can be by any suitable means in the field, for example, by electrical wires (not shown). In operation, the bridge 500 is a powered hardware interface that allows a user to control treatment cycles of the thermal treatment units 100. For example, there may be a single 15-minute heat therapy treatment or a 5-minute cold therapy.

In a preferred embodiment, the controller 502 is a second PCB. In some embodiments, the button 510 and the light 512 may be fixed to the second PCB 502. In such embodiments, the second PCB 502 may be electrically connected to the first PCB 440, for example, by wire through the hollow 401 connector. The power input port 530 may be fixed to the second PCB 502. In such embodiments, the power from the power input port 530 is sent through the second PCB 502 to the first PCB 440 for charging the battery 420 and control signal is also sent from the second PCB 502 to the first PCB 440. When no external power is provided at the power input port 530, the second PCB 502 may receive power from at least one of the batteries 420 from the two thermal treatment units.

The button 510 may be a switch or selector and can be used for selectively activating the heating or cooling of the thermal treatment units, for controlling charging the battery within the treatment units, and for deactivating the heating or cooling of the treatment units. For example, depression of the push button 510 may send signal to the first PCB 440 of at least one of thermal treatment units 100 to activate the preheating (or precooling) sequence or programs of the thermal treatment units 100. The activation of the sequence may be indicated with a one-motor vibration generated by the motor 410 in the thermal treatment unit 100. This may be followed by a two-motor vibration that indicates that therapeutic temperature of the thermal treatment unit 100 has been reached and a three motor vibration when the heat or cooling therapy has completed. The push button 510 can be depressed again at any time to stop the treatment, which immediately stops the therapeutic heat (or cooling) application. As well, the indicator light 512 may be used for indicating activation of the thermal treatment, the status of the thermal treatment and charging of the thermal treatment units by the lights 512 changing color and/or flashing in different patterns. In some embodiments, the second PCB 502 is configured to store pre-determined heating and/or cooling sequences that the user can choose from by pressing the button 510. In embodiments in which the button 510 is fixed to the second PCB 502, the operation of the button 510 and light 512 described above may be realized through the second PCB 502 by the second PCB 502 providing suitable control mechanisms.

FIGS. 5 to 10 show another embodiment of the eye thermal compress assembly 1010 according to the present disclosure. The eye thermal compress assembly 1010 includes two thermal treatment units 1100 connected by a bridge 1500. Each thermal treatment unit 1100 may include upper shell 404, heatsink 430, lower shell 405, mounting board 450, battery 420, component 470, thermoelectric cooler (TEC) 460, and first PCB 440. Pin connection component 490 may be used to connect TEC 460 to first PCB 440 by an electrical wire 1441.

Figure 7:
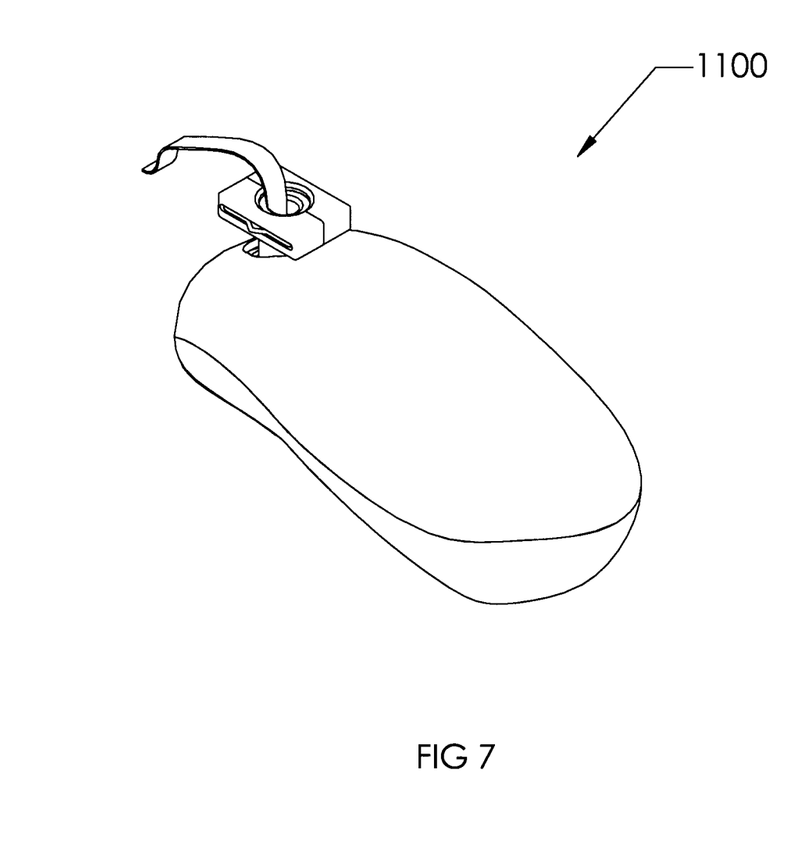
FIG. 7 is a perspective view of the thermal treatment unit in isolation according to an embodiment.
Figure 8:
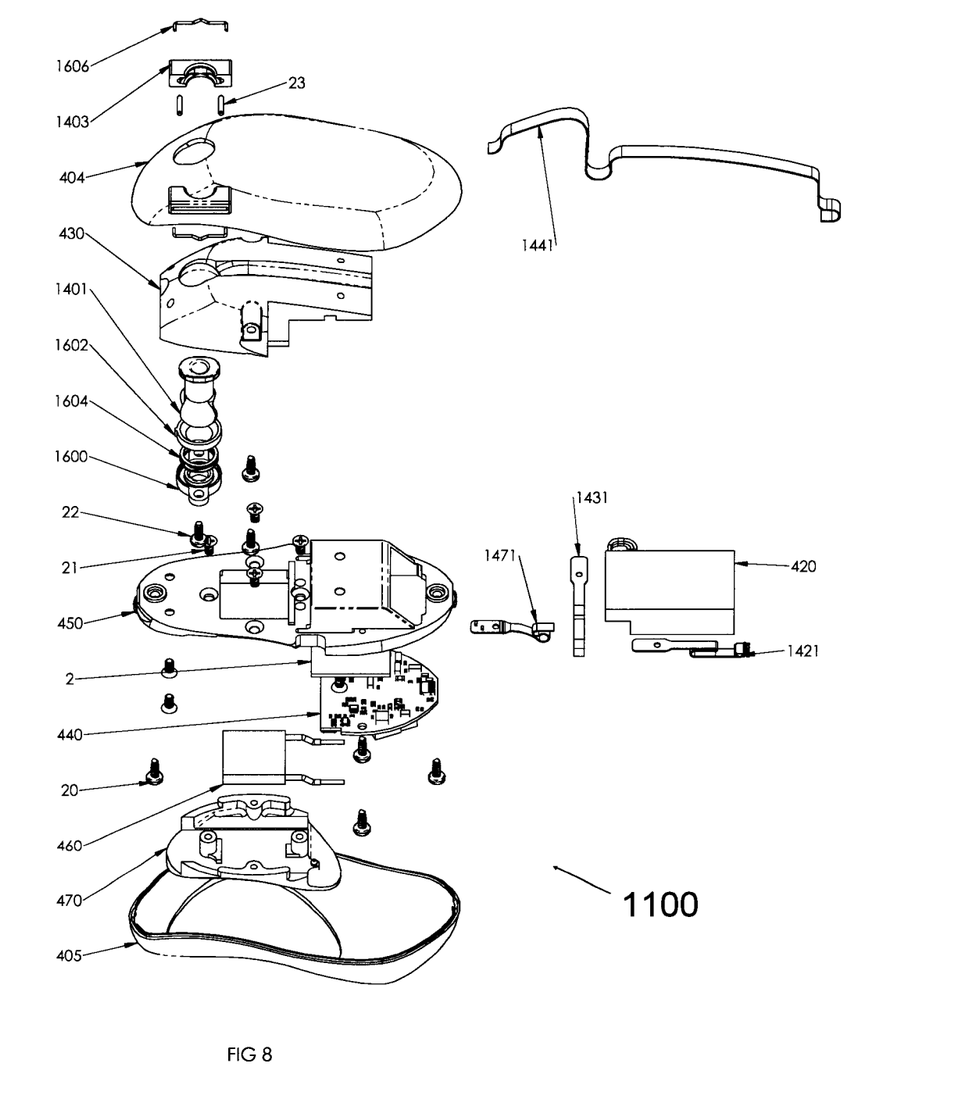
FIG. 8 is an exploded view the thermal treatment unit of FIG. 7.

Each thermal treatment unit 1100 may further comprise a first receptacle 1402, a ball joint 1401, and a second receptacle 1403. Ball joint 1401 includes a first and second opposed ends and defines a wire channel dimensioned to allow passage of electrical wire 1441 therethrough.

First receptacle 1402 is configured to receive first end of ball joint 1401 and comprises a ball joint retainer 1600, a ball joint friction plate 1602 and a wave disk spring 1604. Wave disk spring 1604 may be received in a channel formed in ball joint retainer 1600. Ball joint friction plate 1602 and wave disk spring 1604 cooperate to provide for increased resistance of the first end of ball joint 1401 when it is inserted into first receptacle 1402.

Second receptacle 1403 is configured to receive second end of ball joint 1401. Second receptacle 1403 may be rectangular with chamfered edges or may be trapezoid with beveled edges. A spring 1606 may be provided to increase resistance of the second end of the ball joint 1401 when it is inserted into second receptacle 1403.

Each thermal treatment unit 1100 may further comprise additional components for appropriate temperature control such a heatsink thermistor 1431, a component thermistor 1471, and a battery thermistor 1421.

Figure 9:
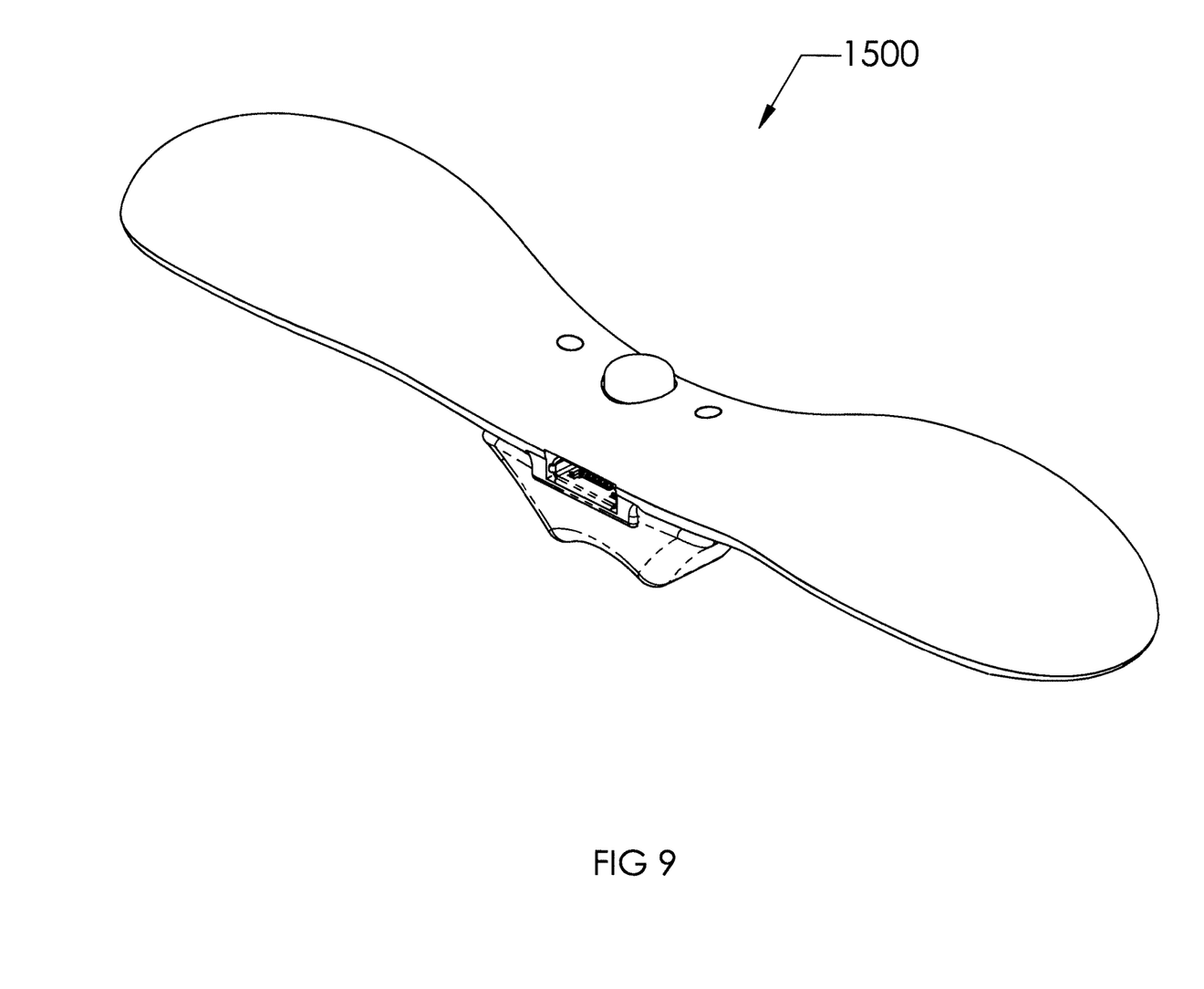
FIG. 9 is a perspective view of the bridge according to an embodiment.
Figure 10:
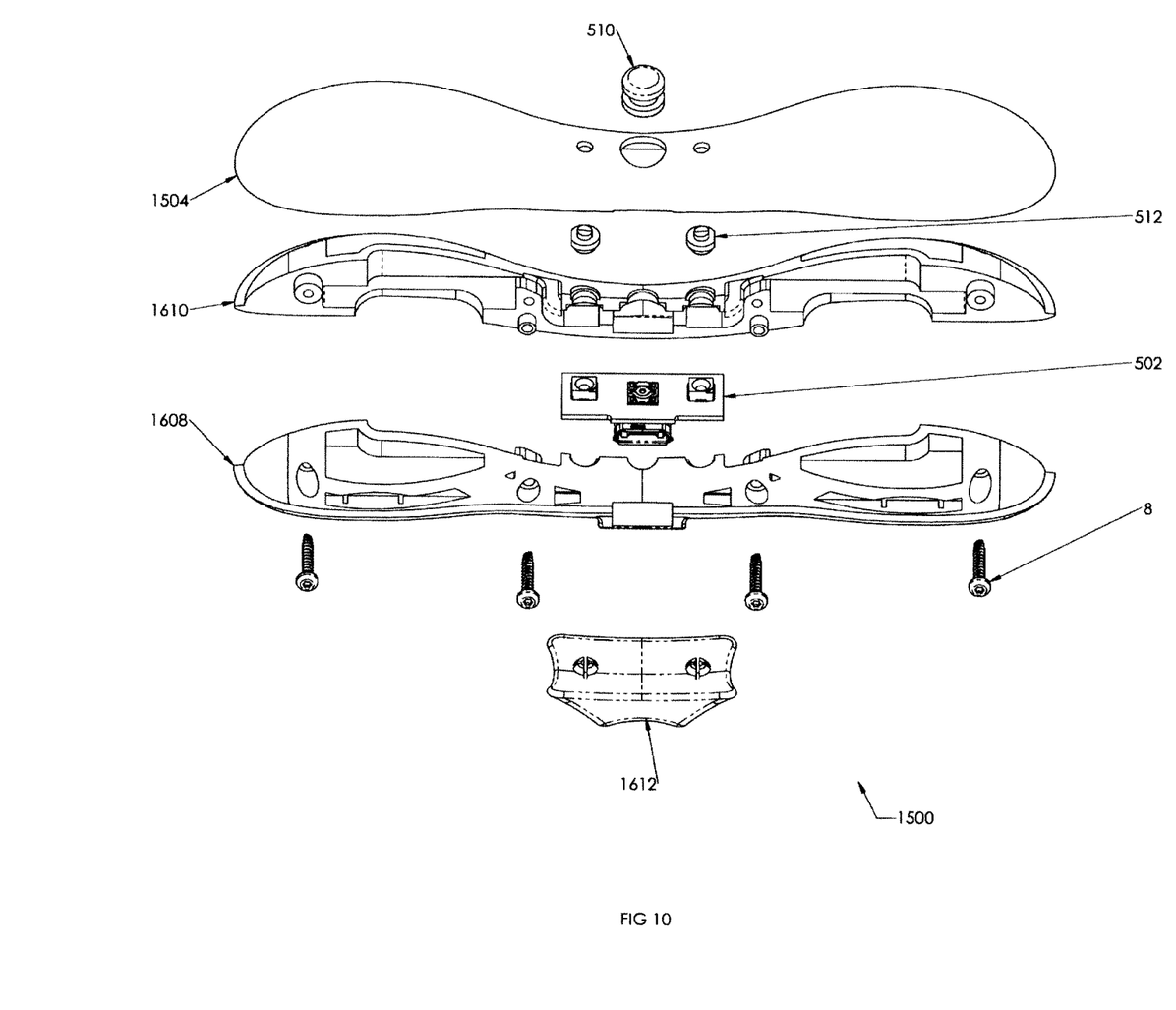
FIG. 10 is an exploded view the bridge of FIG. 9.

As shown in FIGS. 9 and 10, a bridge 1500 connects the two thermal treatment units 1100. Bridge 1500 comprises an upper shell 1504, a lower shell 1503, and PCB 502 enclosed by upper 1503 and lower shell 1503. Lower shell 1503 may comprise a first frame 1608 and a second frame 1610. Frame 1608 and 1610 are configured to matingly combined with each other to form lower shell 1503.

Lower shell 1503 may be configured provide a support structure for PCB 502. Formed in lower shell 1503 are grooves 1612 dimensioned to receive second receptacle 1403 so as to permit sliding movement of second receptacle 1403 therein. Formed in at least one of frame 1608 or 1610 is a power input port 1530 for receiving an electrical cord (not shown) to connect PCB 502 of bridge 1500 with a source of electrical power for charging battery 420.

Bridge 1500 may further comprise a nose piece 1612 configured for placement onto the nose when assembly 1010 is in use. As shown, nose piece 1612 may be removeably secured to lower shell 1503. For additional comfort, the positioning of nosepiece 1612 may be adjusted to accommodate different shaped and sized noses as necessary.

Once a preheating (or precooling) sequence has been activated and the two thermal treatment units 100 or 1100 have reached the desired temperature, the two thermal treatment units 100 or 1100 are placed over the closed eyelids. Alternatively, the eye thermal compress assembly can first be put on the eyelids of the user lying face up and then gradually heating or cooling to the desired temperature.

Variations may be made to some example embodiments, which may include combinations and sub-combinations of any of the above. The various embodiments presented above are merely examples and are in no way meant to limit the scope of this disclosure. Variations of the innovations described herein will be apparent to persons of ordinary skill in the art having the benefit of the example embodiments, such variations being within the intended scope of the present disclosure. In particular, features from one or more of the above-described embodiments may be selected to create alternative embodiments comprised of a sub-combination of features which may not be explicitly described above. In addition, features from one or more of the above-described embodiments may be selected and combined to create alternative embodiments comprised of a combination of features which may not be explicitly described above. Features suitable for such combinations and sub-combinations would be readily apparent to persons skilled in the art upon review of the present disclosure as a whole. The subject matter described herein intends to cover and embrace all suitable changes in technology.

Certain adaptations and modifications of the described embodiments can be made. Therefore, the above discussed embodiments are considered to be illustrative and not restrictive

The invention claimed is:

1. An eye thermal compress assembly comprising:
   two separate and individually controllable and adjustable thermal treatment units for generating thermal energy to provide a heated or cooled treatment surface for eyelids of a user when worn, the thermal treatment units each comprising:
   an upper shell and a lower shell that when coupled form an interior space that houses
   a thermoelectric cooler (TEC) for generating the thermal energy, and
   a heatsink for dissipating the thermal energy into the upper shell, wherein the lower shell of each thermal treatment unit comprises an eye shaped portion for resting against the eyelids of an eye when worn; and
   a bridge connecting the two separate thermal treatment units, the bridge having at least two grooves interspaced from one another and each groove spanning a portion of a longitudinal axis of the bridge;
   wherein each thermal treatment unit is connected to the bridge via a connector, and wherein each groove provided in the bridge receives the respective connector of its associated thermal treatment unit so that the respective connector and respective associated thermal treatment unit are configured to move laterally with respect to the bridge.

2. The eye thermal compress assembly of claim 1, wherein each lower shell is configured for removeably securing a pad between each thermal treatment unit and the eyelids of the user, the pad providing moisture, ointment, pharmacological agent, or any combination thereof to the eyelids.

3. The eye thermal compress assembly of claim 1, wherein a controller is provided in the bridge to store programs of heating and/or cooling.

4. The eye thermal compress assembly of claim 3, wherein a switch is provided for choosing one of the programs of heating and/or cooling.

5. The eye thermal compress assembly of claim 1, wherein the bridge comprises a nosepiece for placement on a nose when the eye thermal compress assembly is worn.

6. The eye thermal compress assembly of claim 1, further comprising one or more of the following:
   a motor attached to an inner side of each lower shell for producing a vibration notification,
   a pin connection component, for electrically connecting each TEC to a controller,
   a treatment surface at an exterior surface of each lower shell, and
   a battery within each upper shell and lower shell for powering the associated TEC.

7. The eye thermal compress assembly of claim 1, wherein the treatment surface is made of smooth aluminum.

8. The eye thermal compress assembly of claim 1, wherein each lower shell has a hole therethrough to expose the treatment surface at an exterior surface of the lower shell to the eyelids of the user.

9. The eye thermal compress assembly of claim 8, wherein the treatment surface is made of a smooth metal.

10. The eye thermal compress assembly of claim 9, wherein the smooth metal is selected from a group consisting of steel, stainless steel, copper, silver, gold and aluminum.

11. The eye thermal compress assembly of claim 1, wherein each respective connector is disposed within the interior space of its associated thermal treatment unit, a portion of the respective connector being surrounded by the associated heatsink, wherein the respective connector extends away from the associated heatsink, through an opening in the associated upper shell, and through an opening in the bridge.

12. The eye thermal compress assembly of claim 11, wherein each respective connector extends through an opening in the associated heatsink.

13. The eye thermal compress assembly of claim 11, wherein each respective connector comprises a ring-shaped receptacle connected to a ball of a ball joint.

14. The eye thermal compress assembly of claim 13, wherein a stem of the ball joint extends away from the ring-shaped receptacle towards the grooves in the bridge.

15. The eye thermal compress assembly of claim 14, wherein the opening in each of the associated heat sink, the associated upper shell and the bridge overlap along a direction defined by the stem of each respective connector.

16. The eye thermal compress assembly of claim 1, wherein the grooves in the bridge comprise a second receptacle with a flat sidewall.

17. The eye thermal compress assembly of claim 1, wherein the grooves in the bridge are located between an upper shell of the bridge and a lower shell of the bridge.

18. The eye thermal compress assembly of claim 1, wherein the each respective connector is hollow.

19. An eye thermal compress assembly comprising two separate and individually positionable thermal treatment units configured to generate thermal energy to provide heated or cooled treatment for eyelids of a user, the thermal treatment units each comprising:
   a lower shell comprising a bottom opening, and an insert, wherein the insert comprises a treatment surface, and wherein the treatment surface and the bottom opening are aligned to expose the treatment surface to the eyelids of the user;
   an upper shell comprising an upper opening, wherein a diameter of the upper opening is less than a diameter of the bottom opening;
   a thermoelectric cooler (TEC) configured to direct thermal energy to the insert;
   a heatsink having an upper surface that faces an interior surface of the upper shell;
   a printed circuit board contained between the heatsink and the lower shell;
   a connector, wherein at least a portion of the connector is surrounded by the heatsink, and
   wherein the connector extends away from the heatsink through the upper opening; and
   a bridge connected to an interior lateral portion of each of the thermal treatment units, each end of the bridge having a hole through which each of the connectors respectively extend, wherein the connectors are hollow and comprise one or more wires connecting the printed circuit board to the bridge,
   the bridge having at least two grooves interspaced from one another and each groove spanning a portion of a longitudinal axis of the bridge;
   wherein each thermal treatment unit is connected to the bridge via its respective connector, and
   wherein each groove provided in the bridge receives the respective connector of its associated thermal treatment unit so that the respective connector and the associated thermal treatment unit are configured to move laterally with respect to the bridge.

20. An eye thermal compress assembly comprising:
two separate and individually positionable thermal treatment units for generating thermal energy to provide heated or cooled treatment surfaces for eyelids of a user when worn, the thermal treatment units each comprising:
- an upper shell and a lower shell that when coupled form an interior space, wherein the lower shell comprises an eye shaped portion for resting against the eyelids of the user when worn;
- a thermoelectric cooler (TEC) within the interior space, the TEC configured for generating the thermal energy; and
- a heatsink for dissipating the thermal energy into the upper shell;

a bridge connecting the two separate thermal treatment units; and
a connector disposed within the interior space of each thermal treatment unit, wherein a portion of each respective connector is surrounded by the associated heatsink, and the respective connector extends away from the associated heatsink through an opening in the associated upper shell, and through an opening in the bridge.

* * * * *